United States Patent [19]
Babiarz et al.

[11] Patent Number: 5,213,699
[45] Date of Patent: May 25, 1993

[54] N-ALLYL SUBSTITUTED PHENYLENEDIAMINE STABILIZERS

[75] Inventors: Joseph E. Babiarz, Amawalk; Thelma Spivack, Spring Valley, both of N.Y.

[73] Assignee: Ciba-Geigy Corporation, Ardsley, N.Y.

[21] Appl. No.: 943,382

[22] Filed: Sep. 10, 1992

Related U.S. Application Data

[63] Continuation of Ser. No. 781,047, Oct. 18, 1991, abandoned.

[51] Int. Cl.$^5$ ............................................. C10M 133/02
[52] U.S. Cl. ...................................... 252/50; 252/401; 564/431; 564/433; 564/434
[58] Field of Search .................. 564/431, 433, 434; 252/50

[56] References Cited

U.S. PATENT DOCUMENTS

| | | | |
|---|---|---|---|
| 3,189,650 | 6/1965 | Chenicek | 564/431 |
| 3,196,180 | 7/1965 | Albert | 564/431 |
| 3,211,793 | 10/1965 | Roos | 564/431 |
| 3,461,165 | 8/1969 | Frye | 564/433 |
| 4,031,016 | 6/1977 | Berger et al. | 252/50 |
| 4,824,601 | 4/1989 | Franklin | 252/50 |

OTHER PUBLICATIONS

Chem. Abst. 109, 191960q (1988).

*Primary Examiner*—Ellen McAvoy
*Attorney, Agent, or Firm*—Luther A. R. Hall

[57] ABSTRACT

N-Allyl substituted p-phenylenediamine compounds are very effective antioxidant stabilizers for organic material subject to oxidative or thermal degradation, particularly for lubricant compositions.

7 Claims, No Drawings

N-ALLYL SUBSTITUTED PHENYLENEDIAMINE STABILIZERS

This invention pertains to novel N-allyl and/or N-benzyl derivatives of p-phenylenediamine and their use as antioxidant stabilizers for lubricant compositions. This is a continuation of application Ser. No. 781,047, filed on Oct. 18, 1991, now abandoned.

BACKGROUND OF THE INVENTION

Japanese Sho 63-81145 [Chemical Abstracts 109, 191960q (1988)] describes 2-diallylamino-s-triazine derivatives as antioxidants for rubber compositions. This reference mentions N,N-diallyl-N'-phenyl-phenylenediamine as a coadditive for rubber compositions.

There is no indication in this reference that the instant compounds would exhibit particularly efficacious antioxidant activity in lubricant compositions.

OBJECTS OF THE INVENTION

One object of the instant invention is to provide new N-allyl and/or N-benzyl derivatives of p-phenylenediamine that are effective antioxidants for lubricant compositions.

Another object of the instant invention is to provide lubricants compositions stabilized against the deleterious effects of oxygen or heat by an effective stabilizing amount of an N-allyl and/or N-benzyl derivative of p-phenylenediamine.

DETAILED DISCLOSURE

The instant invention pertains to a compound of formula I

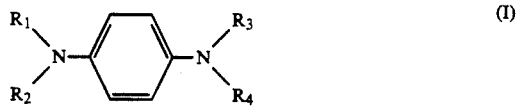

wherein $R_1$, $R_2$, $R_3$ and $R_4$ are independently hydrogen, alkenyl of 3 to 18 carbon atoms, aralkyl of 7 to 15 carbon atoms, aryl of 6 to 10 carbon atoms or said aryl substituted by one to three substituents selected from the group consisting of alkyl of 1 to 20 carbon atoms, cycloalkyl of 5 to 12 carbon atoms, aralkyl of 7 to 15 carbon atoms, —CN, —NO$_2$, halogen, —OR$_5$, —NR$_6$R$_7$, —SR$_8$, —COOR$_9$ and —CONR$_{10}$R$_{11}$ where $R_5$, $R_6$, $R_7$, $R_8$, $R_9$, $R_{10}$ and $R_{11}$ are independently hydrogen, alkyl of 1 to 20 carbon atoms, alkenyl of 3 to 18 carbon atoms, aryl of 6 to 10 carbon atoms, cycloalkyl of 5 to 12 carbon atoms or aralkyl of 7 to 15 carbon atoms;

with the proviso that at least one of $R_1$, $R_2$, $R_3$ or $R_4$ is alkenyl of 3 to 18 carbon atoms or aralkyl of 7 to 15 carbon atoms; and with the further proviso that N,N-diallyl-N'-phenyl-p-phenylenediamine is excluded.

Preferably, the compounds of formula I are those where $R_1$, $R_2$, $R_3$ and $R_4$ are independently hydrogen, allyl, methallyl, benzyl, with the proviso the at least two of $R_1$, $R_2$, $R_3$ or $R_4$ are not hydrogen.

Most preferably, the compounds of formula I are those where at least two of $R_1$, $R_2$, $R_3$ and $R_4$ are allyl or benzyl.

The instant compounds of this invention are conveniently prepared by reaction of p-phenylenediamine or N-phenyl-p-phenylenediamine with an alkenyl or aralkyl halide, such as allyl bromide or benzyl bromide, in the presence of alkali and a quaternary ammonium salt. These intermediates are largely items of commerce.

The instant invention also relates to lubricant compositions, having improved oxidative and thermal stability, which comprises (a) a major amount of a lubricant, subject to oxidative or thermal degradation, and (b) an effective stabilizing amount of a compound of formula I

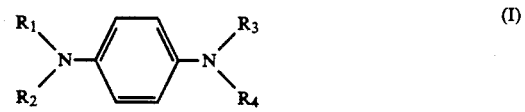

wherein $R_1$, $R_2$, $R_3$ and $R_4$ are independently hydrogen, alkenyl of 3 to 18 carbon atoms, aralkyl of 7 to 15 carbon atoms, aryl of 6 to 10 carbon atoms or said aryl substituted by one to three substituents selected from the group consisting of alkyl of 1 to 20 carbon atoms, cycloalkyl of 5 to 12 carbon atoms, aralkyl of 7 to 15 carbon atoms, —CN, —NO$_2$, halogen, —OR$_5$, —NR$_6$R$_7$, —SR$_8$, —COOR$_9$ and —CONR$_{10}$R$_{11}$ where $R_5$, $R_6$, $R_7$, $R_8$, $R_9$, $R_{10}$ and $R_{11}$ are independently hydrogen, alkyl of 1 to 20 carbon atoms, alkenyl of 3 to 18 carbon atoms, aryl of 6 to 10 carbon atoms, cycloalkyl of 5 to 12 carbon atoms or aralkyl of 7 to 15 carbon atoms;

with the proviso that at least one of $R_1$, $R_2$, $R_3$ or $R_4$ is alkenyl of 3 to 18 carbon atoms or aralkyl of 7 to 15 carbon atoms.

The lubricant of component (a) is particularly a lubricating oil or grease wherein the base medium is a hydrocarbon or synthetic lubricant. The preferred base fluids of this invention include the hydrocarbon mineral oils, olefin fluids, polyolefin fluids, polyether fluids, polyacetals, alkylene oxide polymers, silicone-base fluids and ester fluids. The esters of dicarboxylic acids and monohydric alcohols and the trimethylolpropane and pentaerythritol esters of monocarboxylic acids are particularly of interest. Suitable diesters include the esters of oxalic, malonic, succinic, glutaric, adipic, pimelic, suberic, azelaic and sebacic acids, cyclohexane dicarboxylic acid, phthalic acid, terephthalic acid and the like; and alcohols having 1 to 20 carbon atoms. A commonly used diester is di(2-ethylhexyl) sebacate.

The acids used in forming the trimethylolpropane and pentaerythritol esters include those containing 1 to 30 carbon atoms having straight or branched chain aliphatic, cycloaliphatic, aromatic or alkylated aromatic structures. Mixtures of one or more of such acids may also be used in the preparation of these tri- and tetra-esters. Typical carboxylic acids include, acetic, propionic, butyric, valeric, isovaleric, caproic, caprylic, pelargonic, capric, isodecanoic, lauric, benzoic, nonylbenzoic, dodecylbenzoic, naphthoic, cyclohexanoic and the like. The acids most particularly preferred are pelargonic and commeric valeric acid which contains both n-valeric and isovaleric acids.

The most preferred ester used in this invention is an ester prepared from pentaerythritol, pelargonic, n-valeric and isovaleric acids.

The instant compounds are sufficiently soluble in lubricants to afford the desired antioxidant stabilizing effects. Suitable concentrations range from about 0.001% to about 10% by weight based on the total lubricant composition. Preferably the effective stabilizing amount of the instant compounds is from about 0.1% to about 5% by weight of the total lubricant composition.

The lubricant composition of the instant invention find a wide variety of end uses including engine oils, such as aviation engine oils, automotive engine oils, diesel engine oils, railroad diesel oils, truck diesel oils and the like.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent bright-stocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: G$_1$-OCC-alkylene-COOG$_2$ wherein "alkylene" denotes an alkylene residue having from 2 to 14 carbon atoms and G$_1$ and G$_2$ are the same or different and each is an alkyl group having from 6 to 18 carbon atoms. Tri-esters which are of use as lubricating oil base stocks are those derived from trimethylolpropane and C$_6$–C$_{18}$ mono-carboxylic acids or mixtures thereof, whereas suitable tetra-esters include those derived from pentaerythritol and a C$_6$–C$_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamann, "Schmierstoff und verwandte Produkte", (Verlag Chemie, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of Phenolic Antioxidants

1. Alkylated Monophenols 2,6-Di-tert-butyl-4-methylphenol,2,6-di-tert-butylphenol,2-tert-butyl-4,6-dimethylphenol,2,6-di-tert-butyl-4-ethyl-phenol, 2,6-di-tert-butyl-4-n-butylphenol, 2,6-di-tert-butyl-4-i-butylphenol, 2,6-di-cyclopentyl-4-methylphenol, 2-(β-methylcyclohexyl)-4,6-dimethylphenol, 2,6-di-octa-decyl-4-methylphenol,2,4,6-tri-cyclohexyphenol, 2,6-di-tert-butyl-4-methoxymethyl-phenol, o-tert-butylphenol.

2. Alkylated Hydroquinones 2,6-Di-tert-butyl-4-methoxyphenol, 2,5-di-tert-butyl-hydroquinone, 2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol), 2,2'-thio-bis-(4-octyl-phenyl), 4,4'-thio-bis-(6-tert-butyl-3-methylphenol), 4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or -5-isobutylphenol), 2,2'-methylene-bis-(6-(α-methylbenzyl-4-nonylphenol), 2,2'-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methyl-phenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy-2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5-Di-tert-butyl-4-hydroxyphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate,thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylene-diamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of Amine Antioxidants

N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylene-diamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, di-phenylamine, N-allyldi-phenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoyl-amino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenylamino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1,4-benzothiazine, phenothiazine, N-allyl-phenothiazine, tert-octylated phenothiazine, 3,7-di-tert-octylphenothiazine.

Examples for other Antioxidants

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzo-triazole, salicyclidene-propylene-diamine and salicyclamino-guanidine and salts thereof, 1,2,4-triazole and N,N'-disubstituted aminomethyl triazoles of formula

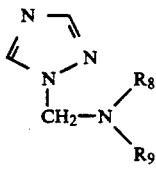

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.
 I. Primary, secondary or tertiary aliphatic or cycloaliphatic amines and amine-salts of organic and inorganic acids, e.g. oil-soluble alkyl-ammonium carboxylates
 II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y-NH_3-R_{10}CO_2-$ in which Y is a group $R_{11}X_1CH_2CH(OH)CH_2$ in which $R_{10}$ and $R_{11}$, independently, are e.g. alkyl and $X_1$ is O, $CO_2$, NH, N(alkyl), N(alkenyl) or S, these salts being prepared by mixing an amine $Y-NH_2$ with an acid $R_{10}CO_2H$, as disclosed in DE-OS 3437 876 (German Offenlegungsschrift).

g) Compounds having the formula $$R_{12}-X_2-CH_2-CH(OH)-CH_2NR_{13}R_{14}$$

in which $X_2$ is $-O-$, $-S-$, $-SO_2-C(O)-O-$ or $-N(Rd)$ in which $R_{12}$ is H or $C_1-C_{12}$alkyl, $R_{13}$ is unsubstituted $C_1-C_4$alkyl or $C_2-C_5$alkyl substituted by one to three hydroxyl groups, $R_{14}$ is hydrogen, unsubstituted $C_1-C_4$alkyl or $C_2-C_5$alkyl substituted by one to three hydroxyl groups provided that at least one of $R_{13}$ and $R_{14}$ is hydroxy-substituted, and $R_{12}$ is $C_2-C_{20}$alkyl $-CH_2-CH(OH)-CH_2NR_{13}R_{14}$ or $R_{12}$ is $C_2-C_{18}$alkenyl, $C_2-C_{18}$alkenyl, $C_2-C_3$alkynyl or $C_5-C_{12}$cycloalkyl provided that, when $X_2$ is $-O-$ or $-C(O)-O-$, $R_{12}$ is branched $C_4-C_{20}$alkyl. These compounds are described in GB Patent Specification 2172284A.

h) Compounds having the formula:

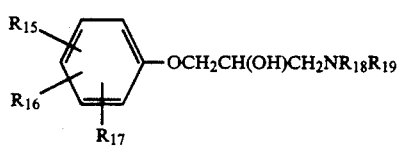

in which $R_{15}$, $R_{16}$, $R_{17}$ are, independently, hydrogen, $C_1-C_{15}$alkyl, $C_5-C_{12}$cycloalkyl, $C_6-C_{15}$aryl or $C_7-C_{12}$aralkyl and $R_{18}$ and $R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each $-CH_2CH_2OH$, $R_{15}$ and $R_{16}$ are not simultaneously hydrogen and $R_{17}$ is not pentyl. These compounds are described in EP Patent specification 0 252 007.

Examples of viscosity-index improvers are:
Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are:
Polymethacrylates, alkylated naphthalene derivatives.

Examples of dispersants/detergents are:

Polybutenylsuccinic acid-amides or -imides, polybutenyl-phosphonic acid derivatives, basic magnesium-, calcium-, and bariumsulfonates and -phenolates.

Examples of anti-wear additives and extreme pressure additives are:

Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The following examples are presented for the purpose of illustration only and are not to be construed to limit the nature or scope of the instant invention in any manner whatsoever.

EXAMPLE 1

N,N,N'-Triallyl-N'-phenyl-p-phenylenediamine

A well-stirred intimate mixture of N-phenyl-p-phenylenediamine (10 g, 0.054 mol), allyl bromide (16 ml, 0.18 mol), potassium iodide (1 g, 0.006 mol) and tetrabutylammonium bromide (1 g, 0.003 mol) is treated with an aqueous solution of sodium hydroxide (7.2 g, 0.18 mol). The mixture is heated to 80° C. for five hours. The mixture is then cooled and extracted with diethyl ether. The organic layer is dried over anhydrous magnesium sulfate and concentrated to an oil. The oil is chromatographed (silica gel; hexane:ethyl acetate) to give the title compound in a yield of 13.1 g (80%) as a yellow oil.

Analysis: Calcd for $C_{21}H_{24}N_2$: C, 82.8; H, 8.0; N, 9.2. Found: C, 82.5; H, 8.1; N, 9.2.

EXAMPLE 2

N,N,-Diallyl-N'-phenyl-p-phenylenediamine

A well-stirred intimate mixture of N-phenyl-p-phenylenediamine (60 g, 0.326 mol), allyl bromide (62 ml, 0.7 mol), potassium iodide (5.2 g, 0.03 mol) and tetrabutylammonium bromide (5.2 g, 0.016 mol) is treated with an aqueous solution of sodium hydroxide (33 g, 0.8 mol). The resulting mixture is stirred at ambient temperature overnight. The mixture is extracted with diethyl ether. The organic fraction is dried and concentrated to an oil. The oil is chromatographed (silica gel; hexane:ethyl acetate) to give the title compound in a yield of 52.1 g (60%) as a yellow oil.

Analysis: Calcd. for $C_{18}H_{20}N_2$: C, 81.8; H, 7.6; N, 10.6. Found: C, 81.4; H, 7.6; N, 10.4.

EXAMPLE 3

N,N'-Dibenzyl-N,N'-diphenyl-p-phenylenediamine

A solution of N,N'-diphenyl-p-phenylenediamine (26 g, 0.1 mol) in toluene (400 ml) is treated sequentially with powdered potassium hydroxide (19.3 g, 0.3 mol), potassium iodide (1.7 g, 0.01 mol) and tetrabutylammonium bromide (1.6 g, 0.005 mol). The resulting mixture is vigorously stirred while benzyl chloride (27.9 g, 0.22 mol) is added dropwise. The mixture is slowly warmed to 90° C. over a one-hour period and then held there for four hours. The mixture is allowed to cool and methylene chloride (100 ml) is added. The resulting mixture is filtered and concentrated to a solid that is washed with water and dried. The title compound is obtained in a yield of 24.8 g (56%) as a tan solid melting at 145°-150° C.

Analysis: Calcd for $C_{32}H_{28}N_2$: C, 87.2; H, 6.4; N, 6.4. Found: C, 87.3; H, 6.6; N, 6.2.

EXAMPLE 4

N,N-Dibenzyl-N'-phenyl-p-phenylenediamine

A well-stirred mixture of N-phenyl-p-phenylenediamine (22.1 g, 0.12 mol) and triethylamine (26.7 g, 0.26 mol) in toluene (300 ml) is treated with benzyl chloride (30.4 g, 0.24 mol). The resulting mixture is warmed to 70°-75° C. for five hours, then cooled and washed with water. The organic fraction is concentrated to an oil that is chromatographed (silica gel; heptane:ethyl acetate) to give the title compound in a yield of 15 g (34%) as a yellow solid melting at 88°-90° C.

Analysis: Calcd for $C_{26}H_{24}N_2$: C, 85.7; H, 6.6; N, 7.7. Found: C, 85.3; H, 6.4; N, 7.5.

EXAMPLE 5

Standard Test Method for Oxidation Stability of Gasoline Engine Oils by Thin-Film Oxygen Uptake (TFOUT)

The antioxidant effectiveness of the instant stabilizers in engine oils is evaluated by the ASTM test method D4742. A 1.5 gram test sample of 10W30 engine oil, formulated to meet SD/CC quality level containing 0.5% by weight of the test compound is placed in the test apparatus. The test is then completed according to the standard method procedure. The oxidation induction time, in minutes, is reported in the table below. A longer induction time indicates a more effective antioxidant.

| Test Compound of | Oxidation Induction Time (minutes) |
| --- | --- |
| Base Oil (no stabilizer) | 113 |
| Example 1 | 300 |
| Example 4 | 227 |

The instant compounds of Examples 1 and 4 are very effective stabilizers for lubricant oils as seen by their long induction times in the TFOUT test.

What is claimed is:

1. A compound of formula I

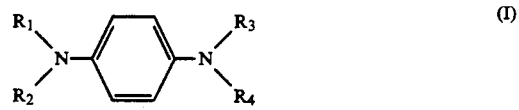

wherein
$R_1$, $R_2$, $R_3$ and $R_4$ are independently hydrogen, allyl or methallyl, aryl of 6 to 10 carbon atoms or said aryl substituted by one to three substituents selected from the group consisting of alkyl of 1 to 20 carbon atoms, cycloalkyl of 5 to 12 carbon atoms, aralkyl of 7 to 15 carbon atoms, —CN, —NO₂, halogen, —OR₅, —NR₆R₇, —SR₈, —COOR₉ and —CONR₁₀R₁₁ where R₅, R₆, R₇, R₈, R₉, R₁₀ and R₁₁ are independently hydrogen, alkyl of 1 to 20 carbon atoms, alkenyl of 3 to 18 carbon atoms, aryl of 6 to 10 carbon atoms, cycloalkyl of 5 to 12 carbon atoms or aralkyl of 7 to 15 carbon atoms;
with the proviso that at least one of $R_1$, $R_2$, $R_3$ or $R_4$ is allyl or methallyl; and with the further proviso that N,N-diallyl-N'-phenyl-p-phenylenediamine is excluded.

2. A compound according to claim 1 wherein at least two of $R_1$, $R_2$, $R_3$ and $R_4$ are allyl or methallyl.

3. A compound according to claim 1 wherein at least two of $R_1$, $R_2$, $R_3$ and $R_4$ are allyl.

4. The compound according to claim 1 which is N,N,N'-triallyl-N'-phenyl-p-phenylenediamine.

5. A stabilized lubricant composition which comprises
   (a) a major amount of a lubricant, subject to oxidative or thermal degradation, and
   (b) an effective stabilizing amount of a compound of formula I

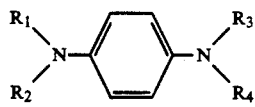 (I)

wherein
$R_1$, $R_2$, $R_3$ and $R_4$ are independently hydrogen, allyl or methallyl, aryl of 6 to 10 carbon atoms or said aryl substituted by one to three substituents selected from the group consisting of alkyl of 1 to 20 carbon atoms, cycloalkyl of 5 to 12 carbon atoms, aralkyl of 7 to 15 carbon atoms, —CN, —NO$_2$, halogen, —OR$_5$, —NR$_6$R$_7$, —SR$_8$, —COOR$_9$ and —CONR$_{10}$R$_{11}$ where $R_5$, $R_6$, $R_7$, $R_8$, $R_9$, $R_{10}$ and $R_{11}$ are independently hydrogen, alkyl of 1 to 20 carbon atoms, alkenyl of 3 to 18 carbon atoms, aryl of 6 to 10 carbon atoms, cycloalkyl of 5 to 12 carbon atoms or aralkyl of 7 to 15 carbon atoms;

with the proviso that at least one of $R_1$, $R_2$, $R_3$ or $R_4$ is ally or methallyl.

6. The composition according to claim 5 wherein the compound of component (b) is N,N-diallyl-N'phenyl-p-phenylenediamine.

7. A composition according to claim 5 wherein the compound of component (b) is N,N,N'-trially-N'-phenyl-p-phenylenediamine.

* * * * *